US011020088B2

(12) United States Patent
Kiyan

(10) Patent No.: US 11,020,088 B2
(45) Date of Patent: Jun. 1, 2021

(54) PROGRAM, METHOD AND DEVICE FOR ULTRASONIC DIAGNOSIS

(71) Applicant: Furuno Electric Co., Ltd., Nishinomiya (JP)

(72) Inventor: Wataru Kiyan, Nishinomiya (JP)

(73) Assignee: Furuno Electric Co., Ltd., Nishinomiya (JP)

( * ) Notice: Subject to any disclaimer, the term of this patent is extended or adjusted under 35 U.S.C. 154(b) by 1154 days.

(21) Appl. No.: 15/027,680

(22) PCT Filed: Sep. 2, 2014

(86) PCT No.: PCT/JP2014/072998
§ 371 (c)(1),
(2) Date: Apr. 6, 2016

(87) PCT Pub. No.: WO2015/053007
PCT Pub. Date: Apr. 16, 2015

(65) Prior Publication Data

US 2016/0242735 A1 Aug. 25, 2016

(30) Foreign Application Priority Data

Oct. 7, 2013 (JP) ............................ JP2013-210183

(51) Int. Cl.
*A61B 8/14* (2006.01)
*A61B 8/08* (2006.01)
*A61B 8/00* (2006.01)

(52) U.S. Cl.
CPC .............. *A61B 8/14* (2013.01); *A61B 8/0858* (2013.01); *A61B 8/5207* (2013.01); *A61B 8/0875* (2013.01); *A61B 8/461* (2013.01)

(58) Field of Classification Search
CPC ....... A61B 8/14; A61B 8/0858; A61B 8/5207; A61B 8/0875
See application file for complete search history.

(56) References Cited

U.S. PATENT DOCUMENTS 6,088,295 A * 7/2000 Altes .................. G01S 15/8904 342/179
6,494,840 B1 * 12/2002 Mak .................... A61B 8/0858 600/443

(Continued)

FOREIGN PATENT DOCUMENTS

JP 2002345821 A 12/2002
JP 2010000126 A 1/2010

(Continued)

OTHER PUBLICATIONS

ISA Japanese Patent Office, International Search Report Issued in Application No. PCT/JP2014/072998, dates Oct. 14, 2014, WIPO, 4 pages.

*Primary Examiner* — Jason M Ip
(74) *Attorney, Agent, or Firm* — Alleman Hall Creasman & Tuttle LLP

(57) ABSTRACT

An ultrasonic diagnosing device is provided, which accurately grasps a state of a detected part even in a case of analyzing the state of the detected part in a percutaneous manner. The ultrasonic diagnosing device includes a level assigning module configured to assign an echo intensity to one of a plurality of levels of echo intensities, the echo intensity being an intensity of each of echo signals respectively corresponding to positions in an area-of-interest, and a characteristic amount calculating module configured to calculate, by targeting two or more of samples having the echo intensities assigned to the plurality of levels by the level assigning module, characteristic amounts indicating a characteristic of the area-of-interest, based on a combination of the echo intensities of the two or more of the samples, the two or more of the samples having a given positional relationship with each other.

12 Claims, 16 Drawing Sheets

ECHO FROM CARTILAGE FRONT SURFACE
ECHO FROM SUBCHONDRAL BONE
SCANNING DIRECTION (SURFACE POSITION)
DEPTH DIRECTION

(56) References Cited

U.S. PATENT DOCUMENTS

| | | | | |
|---|---|---|---|---|
| 2002/0002333 | A1 * | 1/2002 | Angelsen | G01S 7/5205 600/443 |
| 2006/0153451 | A1 * | 7/2006 | Hong | G06T 7/0012 382/173 |
| 2008/0279431 | A1 * | 11/2008 | Kitamura | A61B 1/00009 382/128 |
| 2011/0054313 | A1 * | 3/2011 | Kiyan | A61B 8/0875 600/437 |

FOREIGN PATENT DOCUMENTS

| | | | |
|---|---|---|---|
| JP | 2010017530 | A | 1/2010 |
| JP | 2011050555 | A | 3/2011 |
| JP | 5302578 | B2 | 10/2013 |
| WO | 2014045924 | A1 | 3/2014 |
| WO | 2014103512 | A1 | 7/2014 |

* cited by examiner

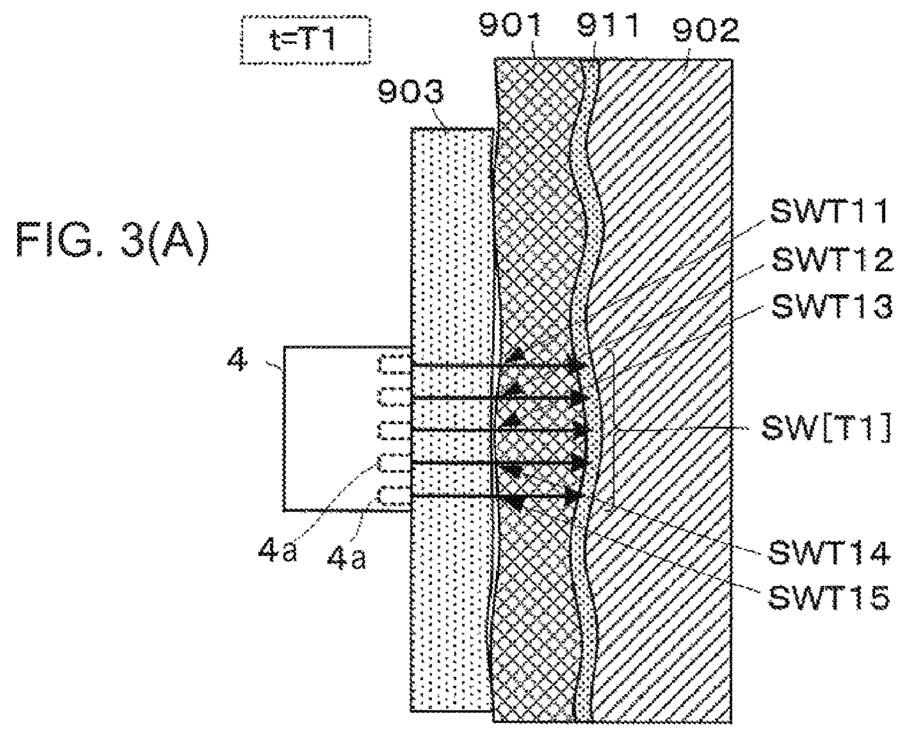
FIG. 3(A)
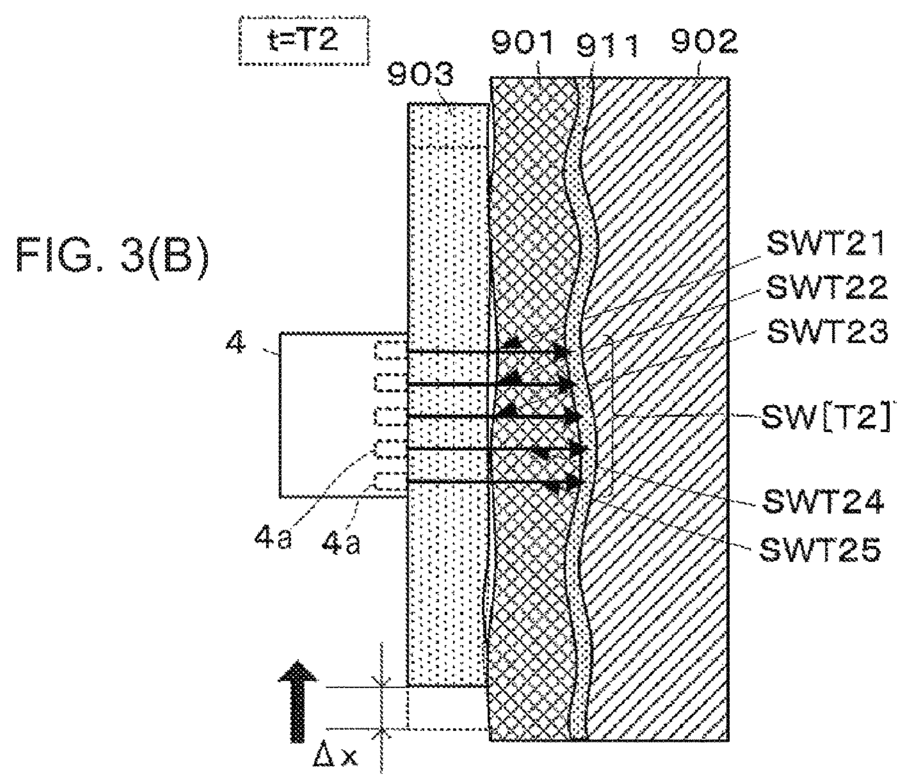
FIG. 3(B)
FIG. 3

PROGRAM, METHOD AND DEVICE FOR ULTRASONIC DIAGNOSIS

TECHNICAL FIELD

This disclosure relates to a program, method and device for ultrasonic diagnosis, which diagnose a state of a detected part that is a detection target in a detected body.

BACKGROUND ART

Conventionally, an ultrasonic diagnosis in which analytical data is generated based on reflection echoes caused by ultrasonic waves transmitted to a detected part, so as to analyze a state of the detected part that is a detection target in a detected body. For example, Patent Document 1 discloses a device which inserts, into a body joint, an endoscope having an ultrasonic wave transmitting and receiving body at a tip end thereof, and calculates a thickness of a cartilage that is a detected part, based on reflection echoes caused by pulse signals transmitted from the ultrasonic wave transmitting and receiving body.

REFERENCE DOCUMENT OF CONVENTIONAL ART

Patent Document

Patent Document 1: JP2002-345821A

DESCRIPTION OF THE DISCLOSURE

Problems to be Solved by the Disclosure

Meanwhile, in a case of analyzing a state of the detected part in a percutaneous manner by using the device described in Patent Document 1, the ultrasonic wave attenuates at a soft tissue. Since the attenuation level of the ultrasonic wave at the soft tissue varies depending on the soft tissue, there is a case where it is difficult to accurately evaluate the state of the cartilage.

This disclosure is made in view of the above situations and aims to accurately grasp a state of a detected part even in a case of analyzing the state of the detected part in a percutaneous manner.

SUMMARY OF THE DISCLOSURE (1) In order to solve the subject described above, according to one aspect of the present disclosure, an ultrasonic diagnosing device for diagnosing a state of a detected part that is a detection target in a detected body is provided. The ultrasonic diagnosing device includes a level assigning module configured to assign an echo intensity to one of a plurality of levels of echo intensities, the echo intensity calculated based on one of echo signals that are caused by ultrasonic signals transmitted from an ultrasonic probe into the detected body, and being an intensity of each of the echo signals that are samples respectively corresponding to positions in an area-of-interest of the detected body, the area-of-interest defined in a depth direction of the detected body and a direction intersecting the depth direction, and a characteristic amount calculating module configured to calculate, by targeting two or more of the samples having the echo intensities assigned to the plurality of levels by the level assigning module, one or more characteristic amounts indicating a characteristic of the area-of-interest, based on a combination of the echo intensities of the two or more of the samples, the two or more of the samples having a given positional relationship with each other.

(2) The ultrasonic diagnosing device may further include an image generating module configured to generate an echo level image configured with a plurality of pixels having luminance levels corresponding to the echo intensities assigned to the plurality of levels by the level assigning module the plurality of pixels associated with the respective positions of the area-of-interest, respectively.

(3) The ultrasonic diagnosing device may further include an upper and lower limit value setting module configured to set an upper limit echo intensity and a lower limit echo intensity, the upper limit echo intensity indicating a highest value among the echo intensities assigned to the plurality of levels, the lower limit echo intensity indicating a lowest value among the echo intensities assigned to the plurality of levels.

(4) The area-of-interest may be designed as an area including echo signals from a front surface of the detected part.

(5) The ultrasonic diagnosing device may further include a co-occurrence matrix generating module configured to generate a co-occurrence matrix based on the echo intensities of the samples respectively corresponding to the positions of the area-of-interest, the echo intensities assigned to the plurality of levels by the level assigning module. The characteristic amount calculating module may calculate the one or more characteristic amounts based on the co-occurrence matrix generated by the co-occurrence matrix generating module.

(6) Moreover, the characteristic amount calculating module may calculate a correlation as one of the one or more characteristic amounts.

(7) Moreover, the co-occurrence matrix generating module may calculate as the co-occurrence matrix, a first co-occurrence matrix targeting pairs of samples corresponding to the area-of-interest, each of the pairs of the samples consisting of a pair of samples having a positional relationship in which the samples are separated by a given distance in the direction intersecting the depth direction. The characteristic amount calculating module may calculate the correlation based on the first co-occurrence matrix.

(8) The characteristic amount calculating module may calculate a contrast as one of the one or more characteristic amounts.

(9) Moreover, the co-occurrence matrix generating module may calculate as the co-occurrence matrix, a second co-occurrence matrix targeting pairs of samples corresponding to the area-of-interest, each of the pairs of the samples consisting of a pair of samples having a positional relationship in which the samples are separated by a given distance in the depth direction. The characteristic amount calculating module may calculate the contrast based on the second co-occurrence matrix.

(10) The ultrasonic diagnosing device may further include a front surface position detecting module configured to detect a position of a front surface of the detected part in the depth direction based on the echo signals, and an area-of-interest designing module configured to design the area-of-interest based on the position of the front surface of the detected part detected by the front surface position detecting module.

(11) Moreover, the level assigning module may include an upper and lower limit value setting module configured to set an upper limit echo intensity and a lower limit echo intensity, the upper limit echo intensity indicating a highest value among the echo intensities assigned to the plurality of levels, the lower limit echo intensity indicating a lowest value among the echo intensities assigned to the plurality of levels. The upper and lower limit value setting module may detect a highest signal value among the echo signals obtained from the front surface of the detected part detected by the front surface position detecting module, and may set the highest signal value as the upper limit value, and the ultrasonic diagnosing device further may include an echo level normalizing module configured to divide the echo intensities at the respective positions of the analysis area by the highest signal value detected by the upper and lower limit value setting module.

(12) The ultrasonic diagnosing device may further include a front surface position correcting module configured to correct positions of the samples corresponding to the area-of-interest in the depth direction so that the position of the front surface of the detected part in the area-of-interest is located within a given range in the depth direction.

(13) The ultrasonic diagnosing device may further include the ultrasonic probe configured to transmit the ultrasonic signals into the detected body, and a display unit configured to display one of the one or more characteristic amounts calculated by the characteristic amount calculating module and an index derived based on the one or more characteristic amounts and indicating the state of the detected part of the detected body.

(14) Moreover, the ultrasonic probe may be capable of transmitting and receiving ultrasonic waves in relation to the area-of-interest defined in the depth direction and a scanning direction of the ultrasonic probe, by scanning along the front surface of the detected body, the scanning direction intersecting the depth direction.

(15) In order to solve the subject described above, according to one aspect of the present disclosure, a method of ultrasonic diagnosis of a state of a detected part that is a detection target in a detected body is provided. The method includes assigning an echo intensity to one of a plurality of levels of echo intensities, the echo intensity calculated based on one of echo signals that are caused by ultrasonic signals transmitted from an ultrasonic probe into the detected body, and being an intensity of each of the echo signals that are samples respectively corresponding to positions in an area-of-interest of the detected body, the area-of-interest defined in a depth direction of the detected body and a direction intersecting the depth direction. The method includes calculating, by targeting two or more of the samples having the echo intensities assigned to the plurality of levels by the assigning the echo intensity to one of the plurality of levels of echo intensities, one or more characteristic amounts indicating a characteristic of the area-of-interest, based on a combination of the echo intensities of the two or more of the samples, the two or more of the samples having a given positional relationship with each other.

In order to solve the subject described above, according to one aspect of the present disclosure, a program for ultrasonic diagnosis of a state of a detected part that is a detection target in a detected body is provided. The program causes a computer to execute assigning an echo intensity to one of a plurality of levels of echo intensities, the echo intensity calculated based on one of echo signals that are caused by ultrasonic signals transmitted from an ultrasonic probe into the detected body, and being an intensity of each of the echo signals that are samples respectively corresponding to positions in an area-of-interest of the detected body, the area-of-interest defined in a depth direction of the detected body and a direction intersecting the depth direction. The program causes a computer to execute calculating, by targeting two or more of the samples having the echo intensities assigned to the plurality of levels by the assigning the echo intensity to one of the plurality of levels of echo intensities, one or more characteristic amounts indicating a characteristic of the area-of-interest, based on a combination of the echo intensities of the two or more of the samples, the two or more of the samples having a given positional relationship with each other.

Effects of the Disclosure

According to the present disclosure, even in a case of analyzing a state of a detected part in a percutaneous manner, the state of the detected part can accurately be grasped.

BRIEF DESCRIPTION OF DRAWINGS

FIGS. 3(A) and 3(B) show schematic side views of an area near the knee in the state where the probe is installed thereon, in which Part (A) is a view illustrating a first state and Part (B) is a view illustrating a second state.

MODES FOR CARRYING OUT THE DISCLOSURE

Figure 1:
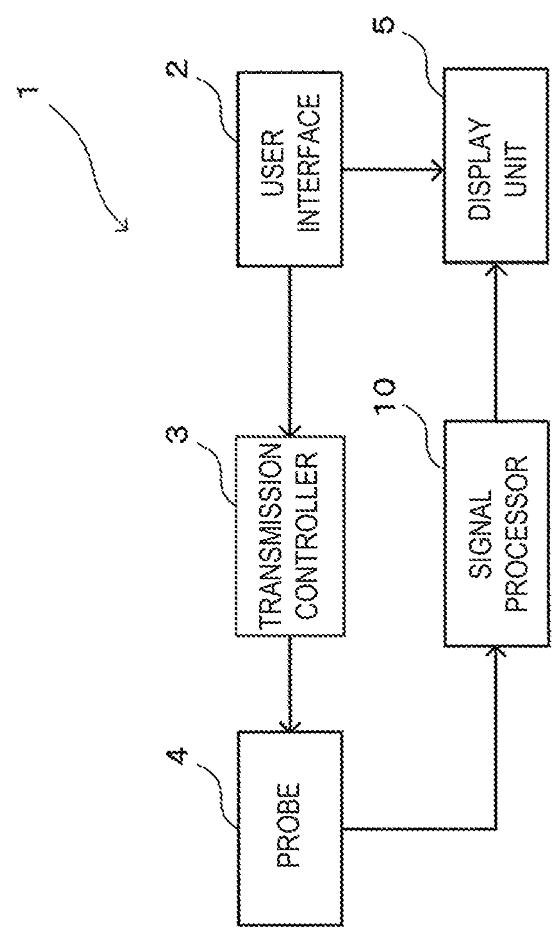
FIG. 1 is a block diagram illustrating a configuration of an ultrasonic diagnosing device according to one embodiment of this disclosure.

A signal processor 10 and an ultrasonic diagnosing device 1 including the signal processor 10 according to one embodiment of this disclosure are described with reference to the drawings. FIG. 1 is a block diagram illustrating a configuration of the ultrasonic diagnosing device 1 according to the embodiment of this disclosure. The ultrasonic diagnosing device 1 diagnoses a state of a cartilage (detected part) of a knee (detected body) of a patient.

Figure 2A:
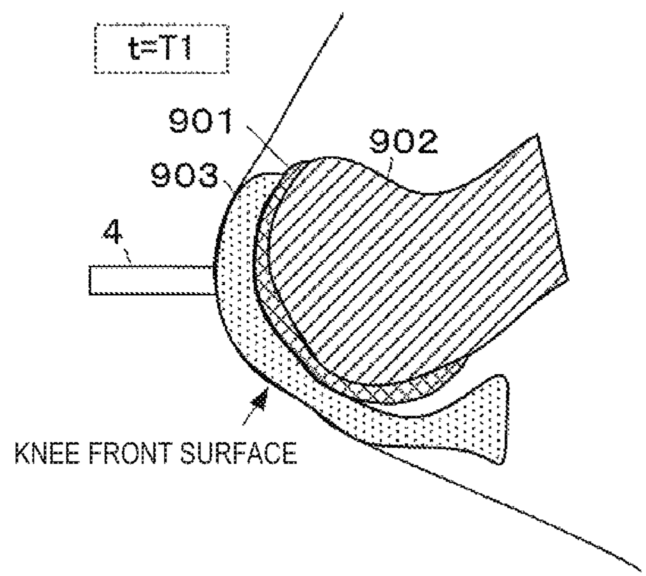
FIGS. 2(A) and 2(B) show schematic views illustrating an installed state of a probe of the ultrasonic diagnosing device on a knee.
Figure 2B:
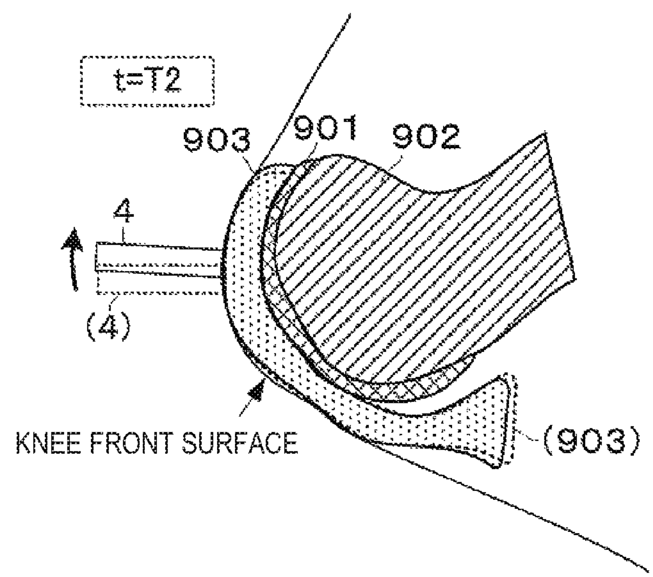

FIGS. 2(A) and 2(B) show schematic views illustrating an installed state of a probe 4 of the ultrasonic diagnosing device 1 according to the embodiment of this disclosure on the detected body. FIG. 2(A) illustrates a case in a first state (t=T1) and FIG. 2(B) illustrates a case in a second state (t=T2).

With the ultrasonic diagnosing device 1, in a state where the probe 4 is made in contact with a front surface of the knee, the probe 4 is moved in up-and-down directions of the knee to switch a relative position thereof to a soft tissue 903 and the cartilage 901, between a position in the first state illustrated in FIG. 2(A) and a position in the second state illustrated in FIG. 2(B). Further, with the ultrasonic diagnosing device 1, ultrasonic waves are transmitted from the probe 4 in each state, and based on echo signals obtained in each state, an index indicating a state of the cartilage 901 (e.g., roughness of the cartilage front surface) is calculated as a numerical value. A user of the ultrasonic diagnosing device 1 (e.g., doctor) looks at the index displayed on a display unit 5 to diagnose the state of the cartilage of a knee joint of the patient.

Overall Configuration

As illustrated in FIG. 1, the ultrasonic diagnosing device 1 includes a user interface 2, a transmission controller 3, the probe 4, the signal processor 10, and the display unit 5.

The user interface 2 is, for example, comprised of one of a keyboard and a touch panel, and receives an operational input from the user. In response to the operational input from the user, the user interface 2 commands the transmission controller 3 to start a detection of the cartilage front surface. Further, the user interface 2 outputs a command to set or switch a display mode of the display unit 5 to the display unit 5 in response to the operational input from the user. Note that, the user interface 2 may be incorporated with the display unit 5.

The transmission controller 3 generates pulse-shaped ultrasonic signals. The transmission controller 3 generates the ultrasonic signals in each of the first state [T1] and the second state [T2].

The transmission controller 3 outputs the ultrasonic signals to the probe 4. The probe 4 includes a plurality of oscillators 4*a* arrayed in a direction parallel to a wave transmitting and receiving surface (see FIGS. 3(A) and 3(B)). This array direction of the oscillators 4*a* becomes a scanning direction. The oscillators 4*a* transmit the ultrasonic signals into the detected body, respectively. Each oscillator 4*a* transmits the ultrasonic signal at a given time interval and receives a reflection echo signal caused thereby.

The probe 4 includes the plurality of oscillators 4*a*. As illustrated in FIGS. 2(A) and 2(B), the probe 4 is arranged such that an end surface thereof on the wave transmitting and receiving surface side comes in contact with a front surface of the soft tissue 903 of the knee which is the detected body. Here, as illustrated in FIGS. 3(A) and 3(B), the soft tissue 903 is a part existing on the front surface side of the detected body with respect to the cartilage 901. The cartilage 901 is attached to a subchondral bone 911. The subchondral bone 911 is a tissue coupled to a bone (cancellous bone) 902.

Note that the probe may include only one oscillator. In this case, a moving direction of the oscillator becomes the scanning direction.

The probe 4 is moved along the front surface of the soft tissue 903 as illustrated in FIG 2(B), while being in contact with the front surface as illustrated in FIG. 2(A). Thus, as illustrated in FIGS. 2(A) and 2(B), the soft tissue 903 moves by following the probe 4 while sliding on the front surface of the cartilage 901. The state of FIG. 2(A), which is before the probe 4 is moved, is the first state (t=T1), and the state of FIG. 2(B), which is after the probe 4 is moved, is the second state (t=T2). Here, the probe 4 is moved in the array direction (scanning direction) of the oscillators.

Each oscillator 4*a* transmits the ultrasonic signal into the detected body in each of the first state [T1] and the second state [T2]. Here, the oscillator 4*a* of the probe 4 transmits the ultrasonic signal such that a direction orthogonal to the front surface of the soft tissue 903 becomes a direction of a center axis of the transmission beam.

Each oscillator 4*a* receives the echo signal caused by the ultrasonic signal reflecting on the soft tissue 903 and the cartilage 901 inside the detected body, and outputs it to the signal processor 10. The probe 4 outputs to the signal processor 10 a first echo group SW[T1] including the echo signals obtained by the oscillators 4*a* in the first state [T1] and a second echo group SW[T2] including the echo signals obtained by the oscillators in the second state [T2].

The signal processor 10 analyzes the state of the cartilage 901 based on the respective echo signals, and outputs the analysis result to the display unit 5. Specific configuration and operation of the signal processor 10 are described later in detail.

The display unit 5 displays the analysis result of the cartilage 901 obtained by the analysis at the signal processor 10. Specifically, the display unit 5 displays characteristic amounts as indexes indicating the state of the cartilage, which is calculated by the signal processor 10. The user estimates the state of the cartilage 901 of the knee of the patient based on the characteristic amounts.

Configuration of Signal Processor

Figure 4:
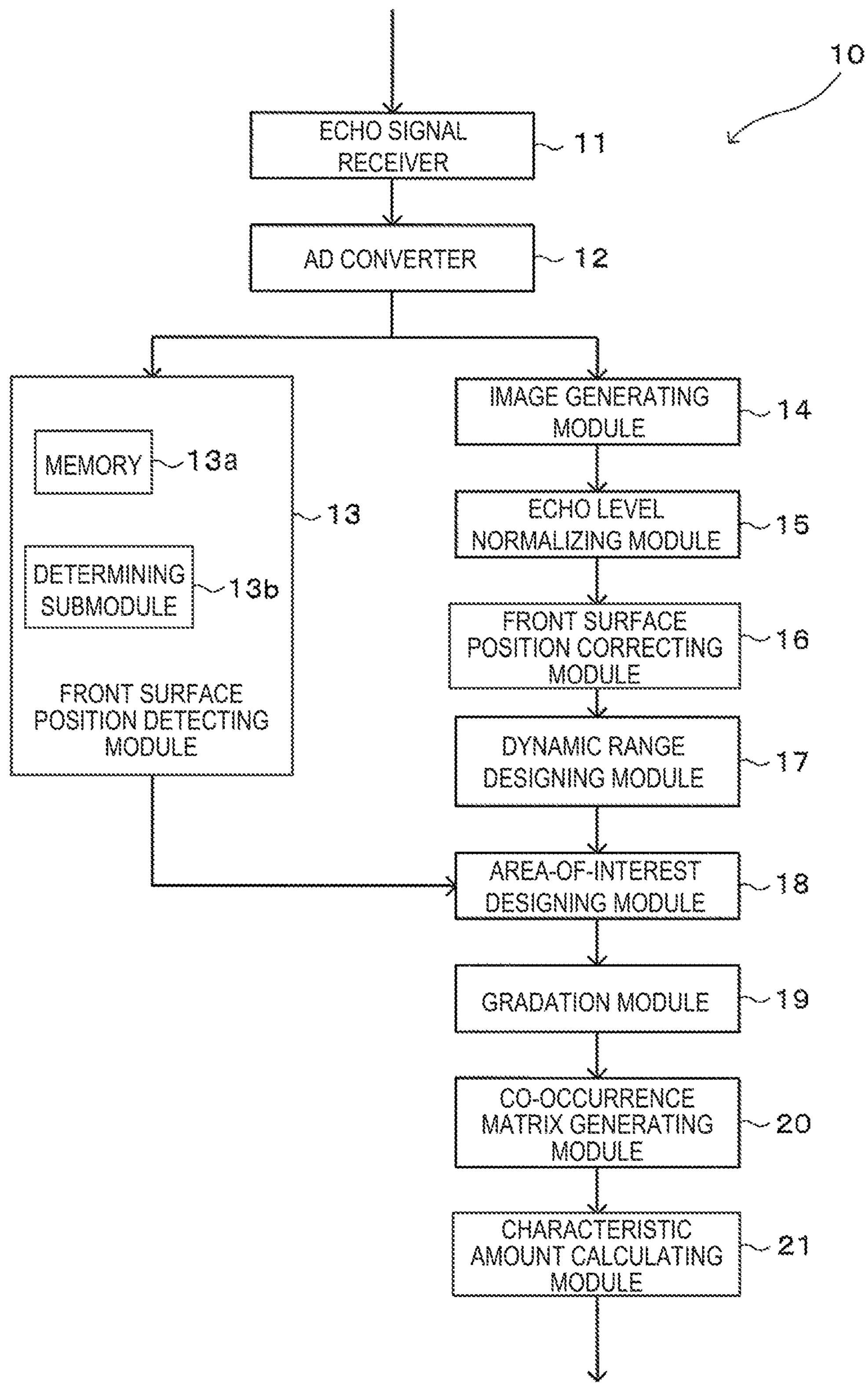
FIG. 4 is a block diagram illustrating a configuration of a signal processor of the ultrasonic diagnosing device illustrated in FIG. 1.

FIG. 4 is a block diagram illustrating a configuration of the signal processor 10 of the ultrasonic diagnosing device 1 according to this embodiment. As illustrated in FIG. 4, the signal processor 10 includes an echo signal receiver 11, an AD converter 12, a front surface position detecting module 13, an image generating module 14, an echo level normalizing module 15, a front surface position correcting module 16, a dynamic range designing module 17, an area-of-interest designing module 18, a gradation module 19, a co-occurrence matrix generating module 20, and a characteristic amount calculating module 21. The signal processor 10 is comprised of hardware including a CPU, a RAM and a ROM (not illustrated). Further, the signal processor 10 is configured by using software including an ultrasonic diagnosing program stored in the ROM.

The ultrasonic diagnosing program is a program that causes the signal processor 10 to implement an ultrasonic diagnosing method according to one embodiment of this disclosure. This program can be installed externally. This program installed is distributed in a state where it is stored in a recording medium, for example. The hardware and the software are configured to operate in cooperation with each other. Thus, the signal processor 10 can function as the echo signal receiver 11, the AD converter 12, the front surface position detecting module 13, the image generating module 14, the echo level normalizing module 15, etc., which are described above.

The echo signal receiver 11 performs a given amplification on each echo signal, and outputs it to the AD converter 12. The echo signal receiver 11 amplifies the respective echo signals individually for each of the first and second echo groups SW[T1] and SW[T2], and outputs them to the AD converter 12.

The AD converter 12 samples each echo signal at a given time interval to discretize data. The echo signal sampled to be the discretized data becomes the echo data. Thus, echo data caused by the data sampling in a depth direction of the detected body at the given time interval can be obtained. The AD converter 12 outputs the echo data to the front surface position detecting module 13 and the image generating module 14.

The front surface position detecting module 13 has a memory 13*a* and a determining submodule 13*b*.

The memory 13*a* has enough volume to store a plurality of echo data obtained in the first state [T1] and a plurality of echo data obtained in the second state [T2]. The memory 13*a* stores the respective echo data outputted by the AD converter 12.

Although specific processing is described later, the determining submodule 13*b* compares waveforms (echo data row in a sweep) obtained from each observed area in the first state [T1], with waveforms (echo data row in a sweep) obtained from each comparison target area in the second state. Based on a result of this comparison, the determining submodule 13*b* detects a position of the comparison target area in the second state to which the selected observed area corresponds.

The determining submodule 13*b* detects a comparison target area in the second state [T2] that is most similar to the observed area in the first state [T1]. The determining submodule 13*b* detects a positional change (whether the position is not changed) of the area where the waveform (or a representative position of the area) is most similar between the first state [T1] and the second state [T2]. Based on a difference in tendency of the positional change of the area, the determining submodule 13*b* identifies an area corresponding to the soft tissue and an area corresponding to the cartilage, and detects a front surface position of the cartilage 901.

Figure 5:
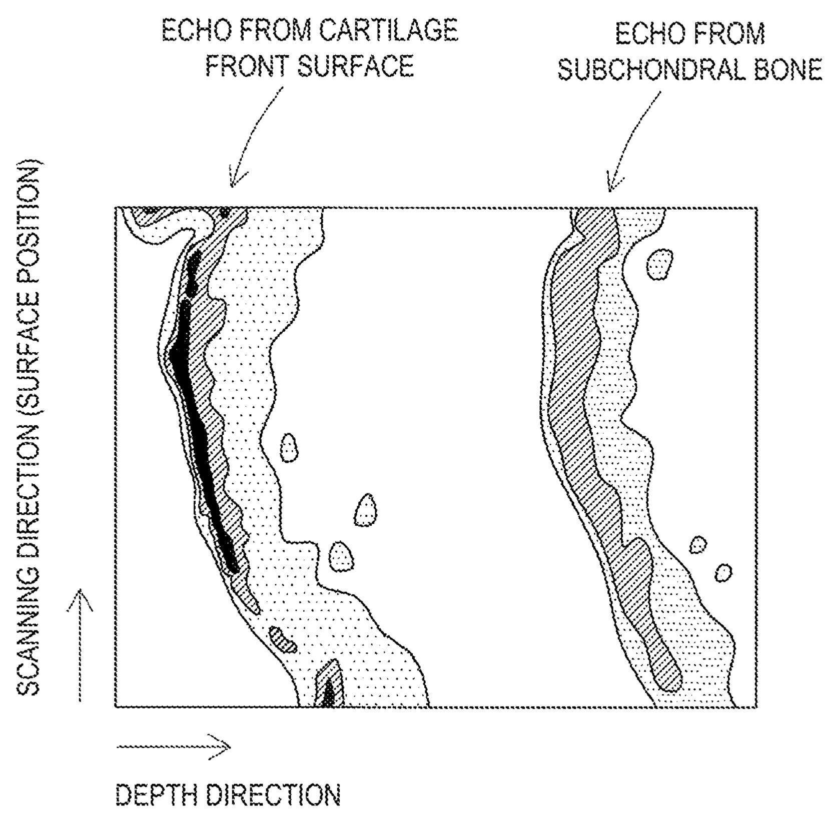
FIG. 5 is a view illustrating an example of an echo level image generated by an image generating module.

FIG. 5 is a view illustrating an example of an echo level image generated by the image generating module 14. Based on the echo data from the AD converter 12, the image generating module 14 generates the echo level image based on echo signals from positions in an analysis area defined in the scanning direction of the ultrasonic probe 4 (a direction intersecting with the depth direction of the detected body) and a depth direction of the cartilage 901 (a direction perpendicular to the scanning direction and extending to the inner side of the knee), for example the image illustrated in FIG. 5. The echo level image is configured with a plurality of pixels arrayed in a grid form. Each pixel is disposed at a position of a display screen associated with a corresponding position of the analysis area, and has a luminance level corresponding to an echo intensity at the corresponding position of the analysis area. In this embodiment, for example, the luminance level is displayed in association with color tones which gradually change in an order of red, orange, yellow, green, blue, and dark blue, as the luminance level changes from high to low.

The echo level normalizing module 15 detects an intensity of an echo signal (echo intensity) that is highest among the echo signals from the respective positions of the analysis area, and divides the echo intensities at the respective positions of the analysis area by the highest echo intensity. Specifically, the echo intensities at the respective positions of the analysis area are normalized so that a highest value thereamong becomes 0 dB.

Figure 6:
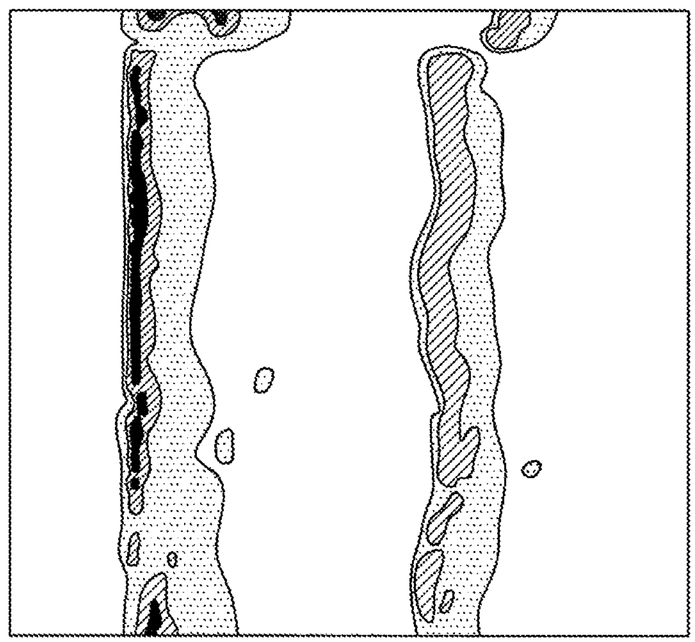
FIG. 6 is a view illustrating an example of an echo level image after a front surface position of a cartilage is corrected.

FIG. 6 is a view illustrating an example of the echo level image after the front surface position of the cartilage 901 is corrected. The front surface position correcting module 16 corrects the front surface position of the cartilage 901 in the echo level image generated by the image generating module 14, so that the front surface position is located within a given range in the depth direction (becomes substantially straight). For example, the front surface position correcting module 16 corrects the front surface position of the cartilage 901 in the echo level image to be substantially straight by suitably performing delay processing on the echo signal corresponding to each front surface position in the scanning direction.

The dynamic range designing module 17 is provided as an upper and lower limit value setting module configured to set an upper limit value (upper limit echo intensity) and a lower limit value (lower limit echo intensity) of the echo intensities at the respective positions of the analysis area. The dynamic range designing module 17 sets the upper limit value to be the highest level value (0 dB) among the signal levels normalized by the echo level normalizing module 15, and designs the lower limit value to be −40 dB for example. The lower limit value (−40 dB) is a value obtained experimentally, and is set to be a value with which a scattering echo in an area starting from the cartilage front surface to the inside of the cartilage can be detected.

Based on the analytical data (the front surface position of the cartilage) calculated by the front surface position detecting module 13, the area-of-interest designing module 18 designs an area having a given length in the depth direction from a given position of the front surface of the cartilage (e.g., about 0.24 mm) and a given length of the front surface in the scanning direction (e.g., about 4 mm), to be an area-of-interest.

Figure 7:
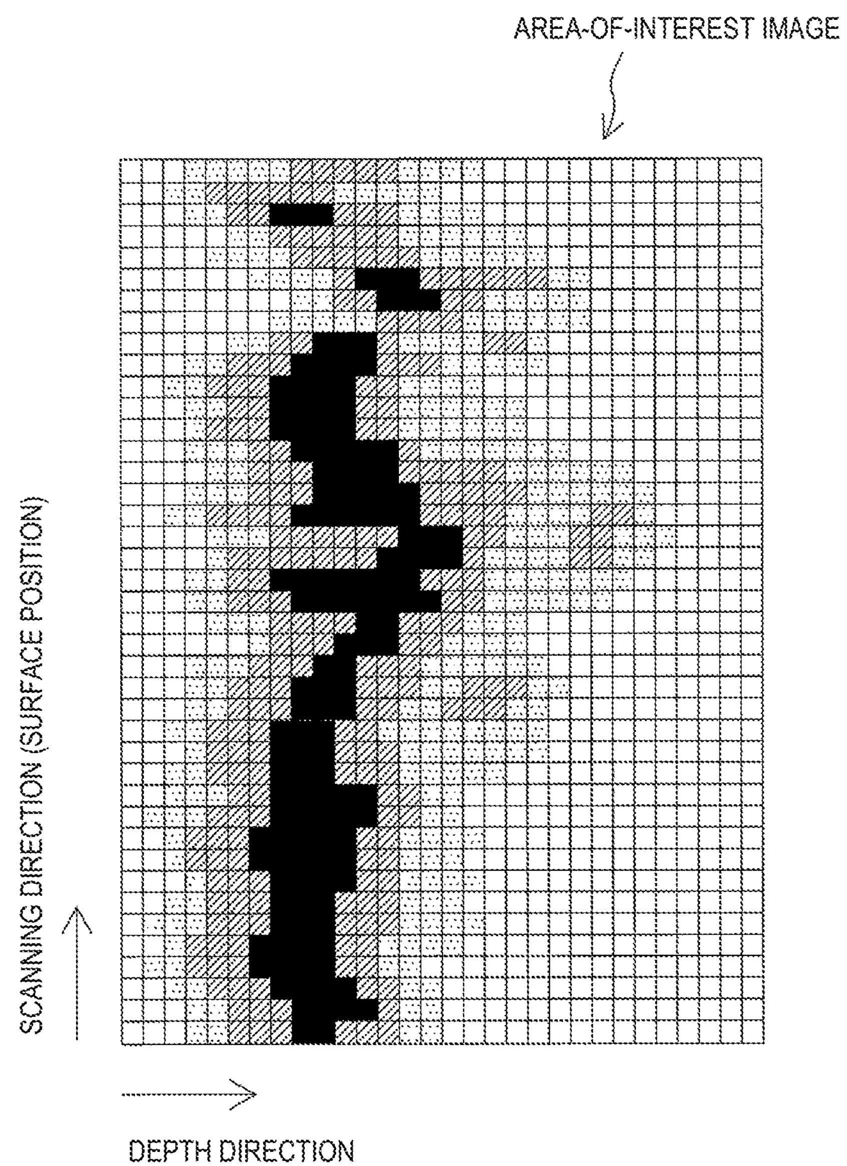
FIG. 7 is a view illustrating an example of an area-of-interest image assigned with gradation.

FIG. 7 is a view illustrating an example of an area-of-interest image assigned with gradation. The gradation module 19 assigns gradation of a plurality of levels (e.g., sixteen tones) to luminance levels of respective pixels of the area-of-interest image that is the echo level image of inside the area-of-interest designed by the area-of-interest designing module 18. Specifically, the gradation module 19 is provided as a level assigning module configured to assign each echo intensity to one of a plurality of levels of echo intensities. Note that, in the example illustrated in FIG. 7, an example of the area-of-interest image assigned with gradation of four tones is illustrated.

Figure 8:
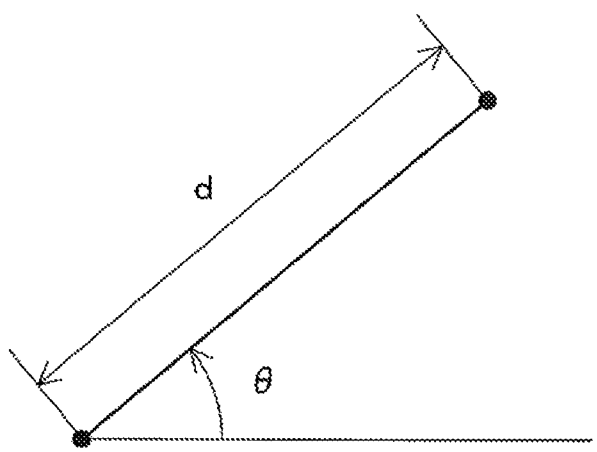
FIG. 8 is a schematic view illustrating a positional relationship between a pair of pixels which are generation targets of a co-occurrence matrix.

The co-occurrence matrix generating module 20 generates a co-occurrence matrix based on the echo level image of inside the area-of-interest in which the luminance levels of the respective pixels are assigned with the gradation of the sixteen tones. The co-occurrence matrix is a matrix of which element is probability $P\delta(i, j)$ $(i, j=1, 2, \ldots, n-1)$ that a pixel located at a position with a certain displacement $\delta=(d, \theta)$ ($d$ is a distance and $\theta$ is an angle, see FIG. 8) from a pixel with a gradient of $i$ has a gradient of $j$. Specifically, the co-occurrence matrix is given by the following Equation 1.

$$P\delta = \begin{bmatrix} P\delta(0, 0) & P\delta(0, 1) & \cdots & \\ P\delta(1, 0) & \ddots & & \\ \vdots & & P\delta(i, j) \end{bmatrix} \tag{1}$$

In this embodiment, the co-occurrence matrix generating module 20 generates two co-occurrence matrixes (a first co-occurrence matrix $P_{d5\theta 90}(i, j)$ and a second co-occurrence matrix $P_{d1\theta 0}(i, j)$). The first co-occurrence matrix $P_{d5\theta 90}(i, j)$ is generated targeting pairs of pixels, each pair separated from each other by five pixels in the scanning direction. Further, the second co-occurrence matrix $P_{d1\theta 0}(i, j)$ is generated targeting pairs of pixels, each pair separated from each other by one pixel in the depth direction. Note that, a value d indicating a distance between the pair of pixels is a preset value based on experiment(s) etc.; however, without limiting to the value described above, it is suitably set according to sizes of the pixels, a beam diameter, a scanning step, a sampling frequency, etc.

The characteristic amount calculating module 21 calculates given characteristic amounts based on the co-occurrence matrixes generated by the co-occurrence matrix generating module 20. In this embodiment, the characteristic amount calculating module 21 calculates a correlation COR and a contrast CNT as the characteristic amounts. Specifically, the characteristic amount calculating module 21 calculates a correlation $COR_{d5\theta 90}$ based on the first co-occurrence matrix $P_{d5\theta 90}(i, j)$ and a contrast $CNT_{d1\theta 0}(i, j)$ based on the second co-occurrence matrix $P_{d1\theta 0}(i, j)$. The correlation COR and the contrast CNT are given by the following Equations 2 and 3.

$$COR = \frac{1}{\sigma_x \sigma_y} \sum_{i=0}^{n-1} \sum_{j=0}^{n-1} \{ijP\delta(i, j) - \mu_x \mu_y\} \quad (2)$$

Note that, $$\mu_x = \sum_{i=0}^{n-1} i \sum_{j=0}^{n-1} P\delta(i, j) \quad (3)$$

$$\sigma_x^2 = \sum_{i=0}^{n-1} (i - \mu_x)^2 \sum_{j=0}^{n-1} P\delta(i, j)$$

$$\mu_y = \sum_{j=0}^{n-1} i \sum_{i=0}^{n-1} P\delta(i, j)$$

$$\sigma_y^2 = \sum_{j=0}^{n-1} (j - \mu_y)^2 \sum_{i=0}^{n-1} P\delta(i, j)$$

$$CNT = \sum_{i=0}^{n-1} \sum_{j=0}^{n-1} \{(i - j)^2 P\delta(i, j)\}$$

Figure 9:
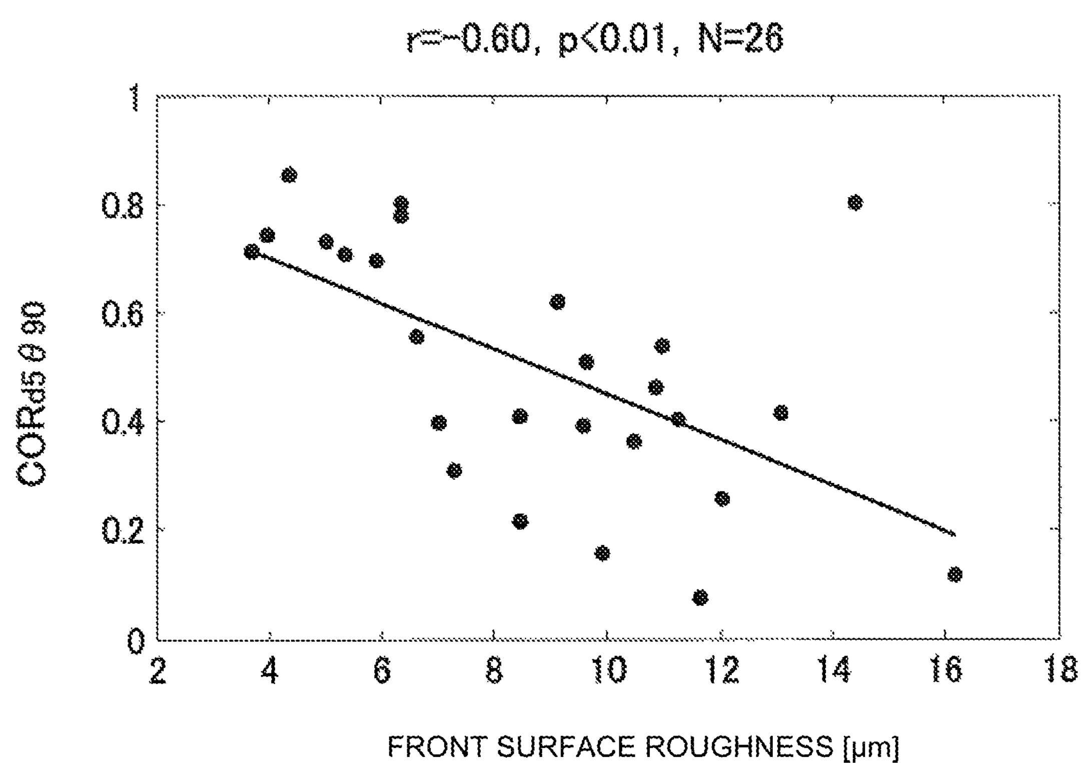
FIG. 9 is a chart used to calculate a correlation coefficient between a correlation $COR_{d5\theta90}$ and a front surface roughness of the cartilage.

FIG. 9 is a chart used to calculate a correlation coefficient between the correlation $COR_{d5\theta 90}$ calculated based on Equation 2 and the front surface roughness of the cartilage, targeting a plurality of samples (N=26). As illustrated in FIG. 9, a comparatively negatively-high correlation was found between the correlation $COR_{d5\theta 90}$ in the direction parallel to the cartilage front surface and the front surface roughness. A cause of the negative correlation can be considered to be that the echo intensity is substantially even in an in-plane direction (a direction where θ=90°) of the cartilage front surface when the cartilage has low degeneration degree (cartilage with low roughness), while the echo intensity varies in the in-plane direction of the cartilage front surface when the cartilage has high degeneration degree (cartilage with high roughness). Therefore, it can be estimated that the degeneration degree of the cartilage is low when the correlation $COR_{d5\theta 90}$ calculated by the characteristic amount calculating module 21 is high, and the degeneration degree of the cartilage is high when the correlation $COR_{d5\theta 90}$ is low.

Figure 10:
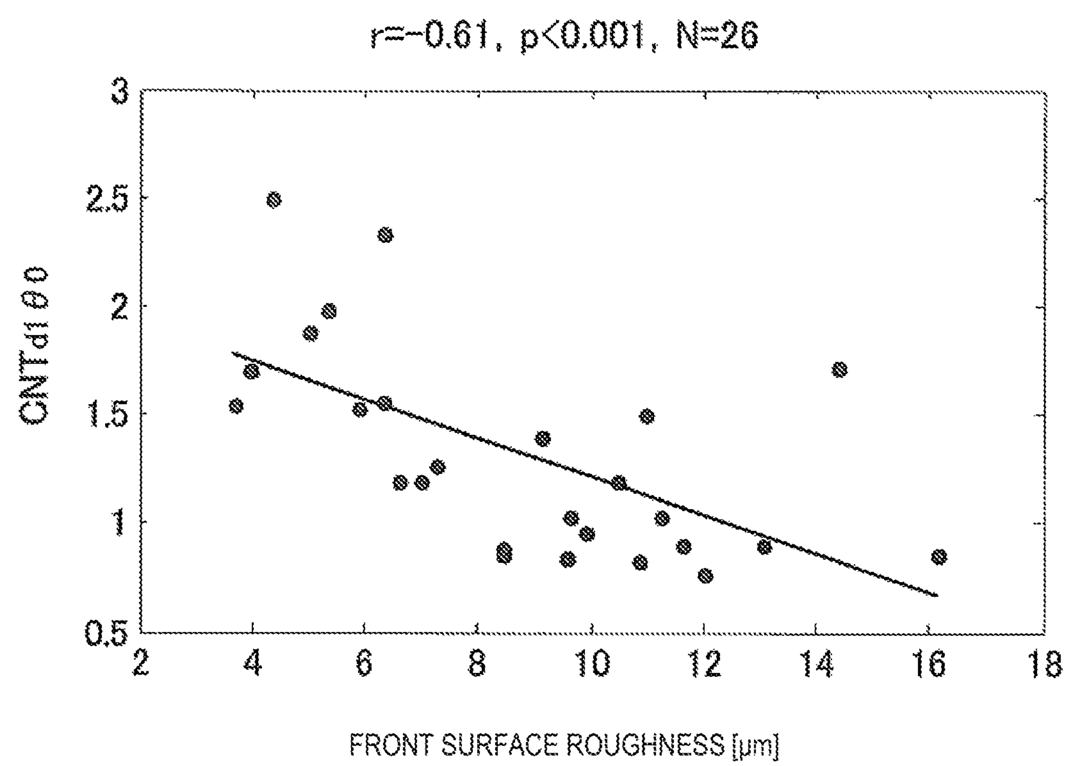
FIG. 10 is a chart used to calculate a correlation coefficient between a contrast $CNT_{d1\theta0}$ and the front surface roughness of the cartilage.

FIG. 10 is a chart used to calculate a correlation coefficient between the contrast $CNT_{d1\theta 0}$ calculated based on Equation 3 and the front surface roughness of the cartilage, targeting the plurality of samples (N=26). As illustrated in FIG. 10, a comparatively negatively-high correlation was found between the contrast $CNT_{d1\theta 0}$ in the direction perpendicular to the cartilage front surface and the front surface roughness. A cause of the negative correlation can be considered to be that the echo intensity changes dramatically in the depth direction from the echo intensity at the cartilage front surface when the cartilage has low degeneration degree, while the echo intensity is less likely to change dramatically when the cartilage has high degeneration degree. Therefore, it can be estimated that the degeneration degree of the cartilage is low when the contrast $CNT_{d1\theta 0}$ calculated by the characteristic amount calculating module 21 is high, and the degeneration degree of the cartilage is high when the contrast $CNT_{d1\theta 0}$ is low.

Operation of Signal Processor

Figure 11:
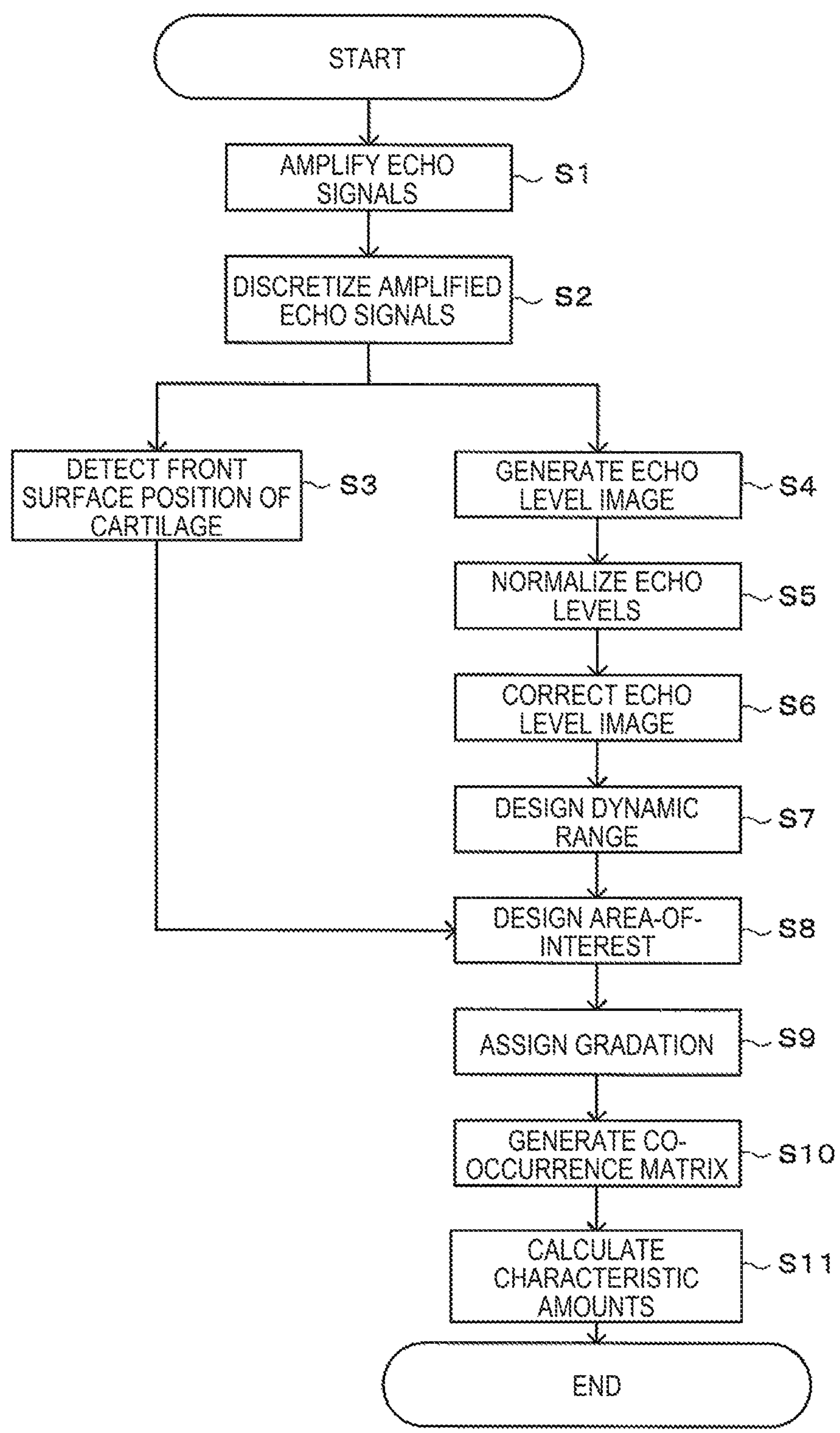
FIG. 11 is a flowchart illustrating operation of the signal processor.

FIG. 11 is a flowchart illustrating the operation of the signal processor 10. The operation of the signal processor 10 is described with reference to FIG. 11.

First at S1, the echo signal receiver 11 amplifies the respective echo signals individually for each of the first and second echo groups SW[T1] and SW[T2], and outputs them to the AD converter 12.

Next at S2, the AD converter 12 samples each of the echo signals in the first and second echo groups SW[T1] and SW[T2] at the given time interval to discretize the data. The AD converter 12 outputs each discretized echo data to the front surface position detecting module 13, and outputs the echo data of one of the two echo groups to the image generating module 14.

Next at S3, the front surface position detecting module 13 detects the front surface position of the cartilage 901. Here, a more specific method of detecting the cartilage front surface, which is implemented by the front surface position detecting module 13 at S3, is described with reference to FIGS. 3 and 12. Note that, to simplify the description, a moving distance Δx of the probe 4 (oscillators 4*a*) between the first and second states [T1] and [T2] is described to be in match with the arrangement interval of the oscillators.

First, as the first state [T1], the probe 4 is made in contact with the front surface of the knee in a state where the knee, which is the detected body, is bent at a first angle, for example. In other words, the probe 4 is made in contact with the front surface of the soft tissue 903, which corresponds to the state of FIG. 3(A).

The respective oscillators disposed at the given arrangement interval, transmit the ultrasonic signals to the direction orthogonal to the front surface of the soft tissue 903 (the scanning direction orthogonal to the wave transmitting and receiving surface). In the example of FIGS. 3(A) and 3(B), five oscillators are disposed in the probe 4 at an even interval in the scanning direction, and as illustrated in FIG. 3(A), the oscillators disposed at the respective arrangement positions transmit the ultrasonic signals to the direction orthogonal to the front surface of the soft tissue 903. The ultrasonic signals from the respective arrangement positions reflect and scatter at respective depth positions of the soft tissue 903, the cartilage 901, and the subchondral bone 911, and thus, echo signals SWT11, SWT12, SWT13, SWT14 and SWT15 from respective positions which have a given space interval from each other in the scanning direction (the scanning-directional positions) are obtained. The oscillators receive the echo signals, respectively. The echo signal group of these echo signals SWT11, SWT12, SWT13, SWT14 and SWT15 obtained by the respective oscillators is the first echo group SW[T1].

Next, the probe 4 is moved to the direction parallel to the front surface of the soft tissue 903 and parallel to the scanning direction, by the distance Δx in the state where the probe 4 is made in contact with the soft tissue 903, which corresponds the second state [T2] and the state of FIG. 3(B). Here, the soft tissue 903 moves following the movement of the probe 4. Therefore, a relative positional relationship of the wave transmitting and receiving surface of the probe 4 with respective positions of the soft tissue 903 in the scanning direction does not change corresponding to the movement of the probe 4. On the other hand, the cartilage 901 is fixed to the bone 902 via the subchondral bone 911 and, thus, does not move even when the probe 4 is moved. Therefore, a relative positional relationship of the wave transmitting and receiving surface of the probe 4 with respective positions of the cartilage 901 in the scanning direction changes corresponding to the movement of the probe 4.

After shifting to the second state, as illustrated in FIG. 3(B), the ultrasonic signals are transmitted from the respective oscillators of the probe 4 to the direction orthogonal to the front surface of the soft tissue 903 (the scanning direction orthogonal to the wave transmitting and receiving surface). The ultrasonic signals from the respective scanning-directional positions reflect and scatter at respective depth positions of the soft tissue 903, the cartilage 901, and the subchondral bone 911, and thus, echo signals SWT21, SWT22, SWT23, SWT24 and SWT25 from the respective positions which have a given space interval from each other in the scanning direction are obtained. The oscillators receive the echo signals, respectively. The echo signal group of these echo signals SWT21, SWT22, SWT23, SWT24 and SWT25 obtained by the respective oscillators is the second echo group SW[T2].

As described above, the first echo group SW[T1] including the plurality of echo signals SWT11, SWT12, SWT13, SWT14 and SWT15 is acquired before the probe 4 is moved. Further, the second echo group SW[T2] including the plurality of echo signals SWT21, SWT22, SWT23, SWT24 and SWT25 is acquired after the probe 4 is moved.

Figure 12:
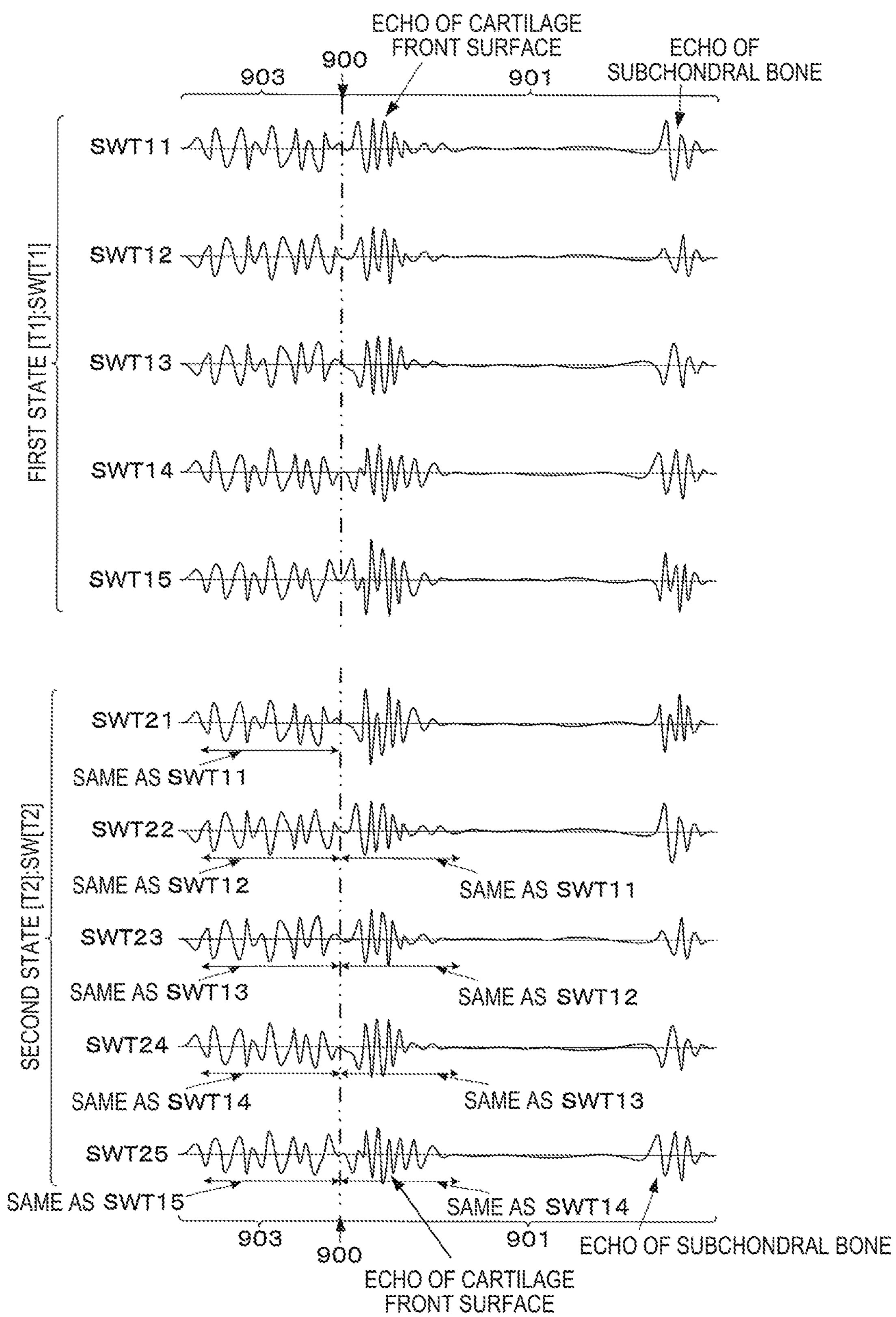
FIG. 12 is a view illustrating an example of waveforms of respective echo signals in the first state [T1] and the second state [T2].

FIG. 12 is a view illustrating an example of waveforms of the respective echo signals in the first state [T1] and the second state [T2]. Note that in FIG. 12, for easier illustration of characteristics of the present disclosure, the distance Δx by which the probe 4 is moved is the same as the space interval between the oscillators, in other words, the interval between the scanning-directional positions. Further in the following description, the detection of the front surface of the cartilage 901 under this condition is described.

(i) Soft Tissue 903

As described above, the probe 4 is made in contact with the front surface of the soft tissue 903 and the soft tissue 903 is not fixed to the front surface of the cartilage 901. Therefore, when the probe 4 is moved by the distance Δx, the soft tissue 903 also moves by the distance Δx, following the movement of the probe 4.

In this case, as indicated by the waveforms of the respective echo signals in the first state [T1] and the waveforms of the respective echo signals in the second state [T2] in FIG. 12, the waveform of the echo signal SWT11 of the first echo group SW[T1] substantially matches with that of the echo signal SWT21 of the second echo group SW[T2] in a portion corresponding to the area of the soft tissue 903.

Similarly, the waveform of the echo signal SWT12 of the first echo group SW[T1] substantially matches with that of the echo signal SWT22 of the second echo group SW[T2] in a portion corresponding to the area of the soft tissue 903. The waveform of the echo signal SWT13 of the first echo group SW[T1] substantially matches with that of the echo signal SWT23 of the second echo group SW[T2] in a portion corresponding to the area of the soft tissue 903. The waveform of the echo signal SWT14 of the first echo group SW[T1] substantially matches with that of the echo signal SWT24 of the second echo group SW[T2] in a portion corresponding to the area of the soft tissue 903. The waveform of the echo signal SWT15 of the first echo group SW[T1] substantially matches with that of the echo signal SWT25 of the second echo group SW[T2] in a portion corresponding to the area of the soft tissue 903.

Therefore, in the soft tissue 903, the echo signals at the scanning-directional positions in the first state [T1] substantially match with the echo signals at the scanning-directional positions in the second state [T2], respectively, in terms of the position thereof with respect to the probe 4 in the scanning direction.

(ii) Cartilage 901

Even when the probe 4 is moved, the cartilage 901 does not move. Therefore, when the probe 4 is moved by the distance Δx, the relationship between the position of each oscillator of the probe 4 (each scanning-directional position) and a corresponding position of the cartilage 901 shifts by the distance Δx in the scanning direction.

In this case, as indicated by the waveforms of the respective echo signals in the first state [T1] and the waveforms of the respective echo signals in the second state [T2] in FIG. 12, the waveform of the echo signal SWT11 of the first echo group SW[T1] does not match with that of the echo signal SWT21 of the second echo group SW[T2] in a portion corresponding to the area of the cartilage 901, but substantially matches with the waveform of the echo signal SWT22 of the second echo group SW[T2] in a portion corresponding to the area of the cartilage 901.

Similarly, the waveform of the echo signal SWT12 of the first echo group SW[T1] substantially matches with that of the echo signal SWT23 of the second echo group SW[T2] in a portion corresponding to the area of the cartilage 901. The waveform of the echo signal SWT13 of the first echo group SW[T1] substantially matches with that of the echo signal SWT24 of the second echo group SW[T2] in a portion corresponding to the area of the cartilage 901. The waveform of the echo signal SWT14 of the first echo group SW[T1] substantially matches with that of the echo signal SWT25 of the second echo group SW[T2] in a portion corresponding to the area of the cartilage 901.

Therefore, in the cartilage 901, the echo signal from each scanning-directional position in the first state [T1] substantially matches with the echo signal from a scanning-directional position in the second state [T2], which is offset from the scanning-directional position in the first state [T1] by the arrangement interval of adjacent oscillators.

As described above, the echo data from the soft tissue 903 and the echo data from the cartilage 901 behave differently from each other in the first and second states [T1] and [T2].

Therefore, by detecting this behavior (a change of a relative position of the observed point between the first and second states), the area of the soft tissue 903 can be differentiated from the area of the cartilage 901. Further, the cartilage front surface, which is a boundary surface of the soft tissue 903 and the cartilage 901 can be detected.

Meanwhile at S4, the image generating module 14 generates the echo level image as illustrated in FIG. 5, based on the echo data outputted from the AD converter 12.

Next at S5, the echo level normalizing module 15 normalizes the echo intensities at the respective positions of the analysis area.

Next at S6, the front surface position correcting module 16 corrects the echo level image so that the front surface position of the cartilage 901 in the echo level image is located within the given range in the depth direction. Note that, if the front surface position of the cartilage 901 in the echo level image is located within the given range in the depth direction, the process at S6 is omitted.

Next at S7, the dynamic range designing module 17 sets the upper limit value to be the highest value (0 dB) among the signal levels normalized by the echo level normalizing module 15, and sets the lower limit value to be −40 dB.

Next at S8, the area-of-interest designing module 18 designs the area having the given length in the depth direction from the given position of the front surface of the cartilage and the given length of the front surface in the scanning direction, to be the area-of-interest.

Next at S9, the gradation module 19 assigns the gradation of the plurality of levels (e.g., sixteen tones) to the luminance levels of the respective pixels of the area-of-interest image which is the echo level image of inside of the area-of-interest designed at S8.

Next at S10, the co-occurrence matrix generating module 20 generates the first co-occurrence matrix $P_{d5\theta90}(i, j)$ and the second co-occurrence matrix $P_{d1\theta0}(i, j)$ based on Equation 1.

Next at S11, the characteristic amount calculating module 21 calculates the correlation $COR_{d5\theta90}$ and the contrast $CNT_{d1\theta0}$ based on the first co-occurrence matrix $P_{d5\theta90}(i, j)$ and the second co-occurrence matrix $P_{d1\theta0}(i, j)$ generated at S10 based on Equations 2 and 3, respectively. The correlation $COR_{d5\theta90}$ and the contrast $CNT_{d1\theta0}$ calculated as above are displayed on the display unit 5 as the numerical values.

Effects

As described above, with the ultrasonic diagnosing device 1 according to this embodiment, without incision of the soft tissue 903 near the knee, the characteristic amounts which are highly correlative with the state of the detected part (the front surface roughness of the cartilage 901 in this embodiment) is calculated based on the intensities of the echo signals which are the samples corresponding to the respective positions of the area-of-interest, and the state of the cartilage can be estimated.

Therefore, with the ultrasonic diagnosing device 1, even in a case of analyzing the state of the cartilage 901 in a percutaneous manner, the state (front surface roughness) of the cartilage 901 can accurately be grasped.

Moreover, with the ultrasonic diagnosing device 1, since the characteristic amounts are calculated based on the echo level image configured with the pixels having the illuminance levels corresponding to the echo intensities of the samples corresponding to the respective positions of the area-of-interest, the characteristic amounts can suitably be calculated.

Moreover, with the ultrasonic diagnosing device 1, the upper limit echo intensity and the lower limit echo intensity are set by the dynamic range designing module 17. Thus, the gradation can suitably be assigned to the respective pixels configuring the echo level image.

Moreover, with the ultrasonic diagnosing device 1, since the area including the echo signals from the cartilage front surface of the knee is designed to be the area-of-interest, the detected part can surely be included in the diagnostic target.

Moreover, with the ultrasonic diagnosing device 1, the characteristic amounts are calculated based on the co-occurrence matrixes calculated by the co-occurrence matrix generating module 20. Thus, the characteristic amounts can suitably be calculated.

Moreover, with the ultrasonic diagnosing device 1, by calculating, as one of the characteristic amounts, the correlation COR highly correlative with the front surface roughness of the cartilage 901, the front surface roughness of the cartilage 901 can suitably be estimated.

Moreover, with the ultrasonic diagnosing device 1, in the area-of-interest image, the correlation $COR_{d5\theta90}$ is calculated based on the first co-occurrence matrix $P_{d5\theta90}$ generated targeting the pairs of pixels, each pair of pixels consisting of a pair of pixels having a positional relationship in which they are separated by a given distance in the scanning direction. As illustrated in FIG. 9, the correlation $COR_{d5\theta90}$ is highly correlative with the front surface roughness. Therefore, by calculating the correlation $COR_{d5\theta90}$, the front surface roughness of the cartilage 901 can more suitably be estimated.

Moreover, with the ultrasonic diagnosing device 1, by calculating, as one of the characteristic amounts, the contrast CNT highly correlative with the front surface roughness of the cartilage 901, the front surface roughness of the cartilage 901 can suitably be estimated.

Moreover, with the ultrasonic diagnosing device 1, in the area-of-interest image, the contrast $CNT_{d1\theta0}$ is calculated based on the second co-occurrence matrix $P_{d1\theta0}$ generated targeting the pairs of pixels, each pair of pixels consisting of a pair of pixels having a positional relationship in which they are separated by a given distance in the depth direction. As illustrated in FIG. 10, the contrast $CNT_{d1\theta0}$ is highly correlative with the front surface roughness. Therefore, by calculating the contrast $CNT_{d1\theta0}$, the front surface roughness of the cartilage 901 can more suitably be estimated.

Moreover, with the ultrasonic diagnosing device 1, the area-of-interest to be the analysis target is designed based on the front surface position of the cartilage 901 detected by the front surface position detecting module. Thus, the area-of-interest can automatically be designed.

Moreover, with the ultrasonic diagnosing device 1, the echo intensities at the respective positions in the echo level image are normalized through dividing them by the highest signal value among the echo signals from the cartilage 901. In this manner, an individual difference of the soft tissue 903 in every detected body can be eliminated, and thus, more accurate characteristic amounts can be calculated for each detected body.

Moreover, with the ultrasonic diagnosing device 1, the echo level image is corrected so that the front surface position of the cartilage 901 in the echo level image is located within the given range in the depth direction. Thus, the front surface position of the cartilage 901 becomes substantially straight in the depth direction, and as a result, the co-occurrence matrix can suitably be generated.

Moreover, with the ultrasonic diagnosing device 1, the characteristic amounts calculated by the signal processor 10 are displayed on the display unit 5. Thus, the user can visually confirm the characteristic amounts as the indexes indicating the degeneration degree of the cartilage 901.

Although the embodiment of this disclosure is described above, this disclosure is not limited to the above, and without deviating from the scope of this disclosure, various modifications may be applied.

Figure 13:
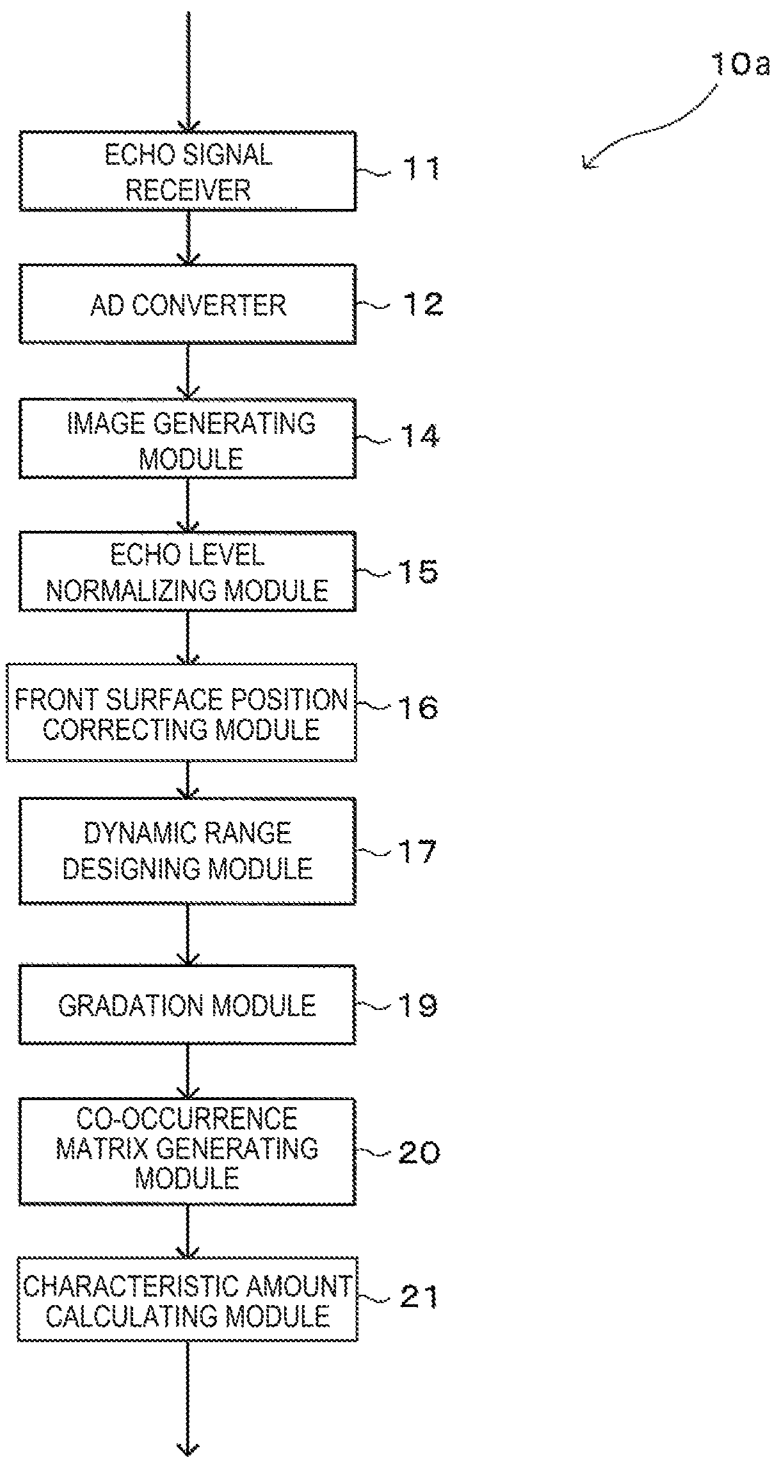
FIG. 13 is a block diagram illustrating a configuration of a signal processor of the ultrasonic diagnosing device according to a modification.

Modifications (1) FIG. 13 is a block diagram illustrating a configuration of a signal processor 10*a* of the ultrasonic diagnosing device according to a modification. The signal processor 10*a* of this modification has a configuration in which the front surface position detecting module 13 and the area-of-interest designing module 18 are omitted from the signal processor 10 of the above embodiment.

With the ultrasonic diagnosing device according to this modification, the echo level image generated by the image generating module 14 is displayed on the display unit 5. Further, the user looks at the echo level image and selects part of the echo level image which includes the cartilage front surface, to be the area-of-interest. Then the signal processor 10 assigns the gradation, generates the co-occurrence matrixes, and calculates the characteristic amounts, sequentially for the area-of-interest image which is the echo level image of inside the area-of-interest. Therefore, by configuring the signal processor 10*a* as this modification, the state (front surface roughness) of the cartilage 901 can accurately be grasped even in the case of analyzing the state of the cartilage 901 in a percutaneous manner, similar to the above embodiment.

(2) In the above embodiment, the contrast $CNT_{d1\theta0}$ is calculated based on the second co-occurrence matrix $P_{d1\theta0}(i, j)$; however, a contrast $CNT_{d5\theta90}$ may be calculated based on the first co-occurrence matrix $P_{d5\theta90}(i, j)$.

Figure 14:
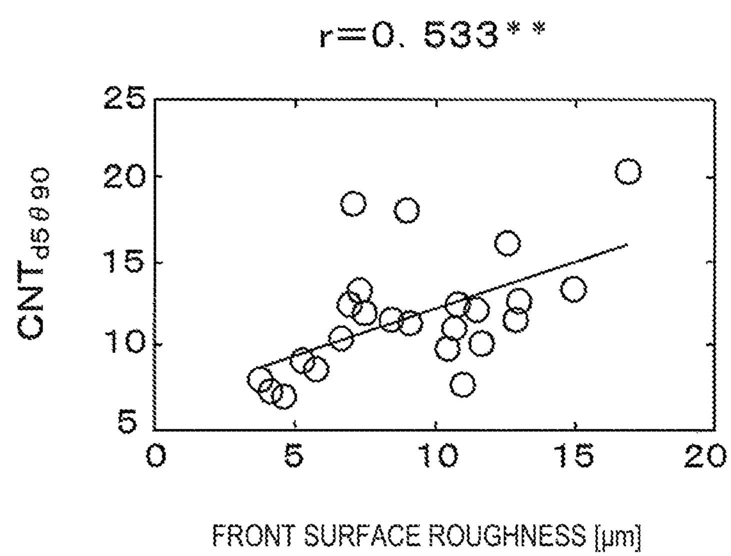
FIG. 14 is a chart used to calculate a correlation coefficient between a contrast $CNT_{d5\theta90}$ and the front surface roughness of the cartilage.

FIG. 14 is a chart used to calculate a correlation coefficient between the contrast $CNT_{d5\theta90}$ calculated based on Equation 3 and the front surface roughness of the cartilage, targeting the plurality of samples. As illustrated in FIG. 14, a positive correlation was found between the contrast $CNT_{d5\theta90}$ in the direction parallel to the cartilage front surface and the front surface roughness. A cause of the positive correlation can be considered to be that the echo intensity is substantially even in the in-plane direction of the cartilage front surface when the cartilage has low degeneration degree, while an area where the echo intensity is locally low exists when the cartilage has high degeneration degree. Therefore, it can be estimated that the degeneration degree of the cartilage is low when the contrast $CNT_{d5\theta90}$ is low, and the degeneration degree of the cartilage is high when the contrast $CNT_{d5\theta90}$ is high.

(3) In the above embodiment, as the characteristic amounts, the correlation COR and the contrast CNT are calculated; however, without limiting to this, other characteristic amounts may be calculated. For example, a local homogeneity IDM, an entropy EPY, a sum average SUMA, a sum variance SUMV, etc. are calculated as characteristic amounts, and the degeneration degree of the cartilage may be estimated based thereon. These characteristic amounts can be given by the following Equations 4 to 7, respectively.

$$IDM = \sum_{i=0}^{n-1}\sum_{j=0}^{n-1} \frac{1}{1+(i-j)^2} P\delta(i, j) \tag{4}$$

$$EPY = \sum_{i=0}^{n-1}\sum_{j=0}^{n-1} P\delta(i, j)\log\{P\delta(i, j)\} \tag{5}$$

-continued $$SUMA = \sum_{i=0}^{n-1}\sum_{j=0}^{n-1} \{(i+j)P\delta(i, j)\} \tag{6}$$

$$SUMV = \sum_{i=0}^{n-1}\sum_{j=0}^{n-1} [\{(i+j)-SUMA\}^2 P\delta(i, j)] \tag{7}$$

(4) In the above embodiment, by moving the probe 4 in the up-and-down directions in the state where it is made in contact with the knee, the position of the probe 4 relative to the soft tissue 903 and the cartilage 901 is changed and the front surface position of the cartilage 901 is detected; however, it is not limited to this. For example, the probe 4 may be fixed and the knee may be bent by a jig etc., so as to change the relative positional relationships of the probe 4 with the soft tissue 903 and the cartilage 901.

(5) In the above embodiment, the depth position detected by the front surface position detecting module 13 is the front surface position of the cartilage 901; however, it is not limited to this. For example, movement averaging processing may be performed along the front surface position detected by the front surface position detecting module 13. Thus, a noise (e.g., spike noise) in the front surface position detection can be smoothened.

(6) In the above embodiment, the numerical values of the characteristic amounts calculated by the characteristic amount calculating module 21 are displayed on the display unit 5 as they are; however, without limiting to this, indexes indicating the degeneration degree of the cartilage derived based on the characteristic amounts may be displayed on the display unit 5. For example, each of the characteristic amounts may be categorized into one of a plurality of ranks corresponding to the numerical value of the characteristic amount, and the ranks (e.g., alphabets, such as A to C) may be displayed on the display unit 5.

Figure 15:
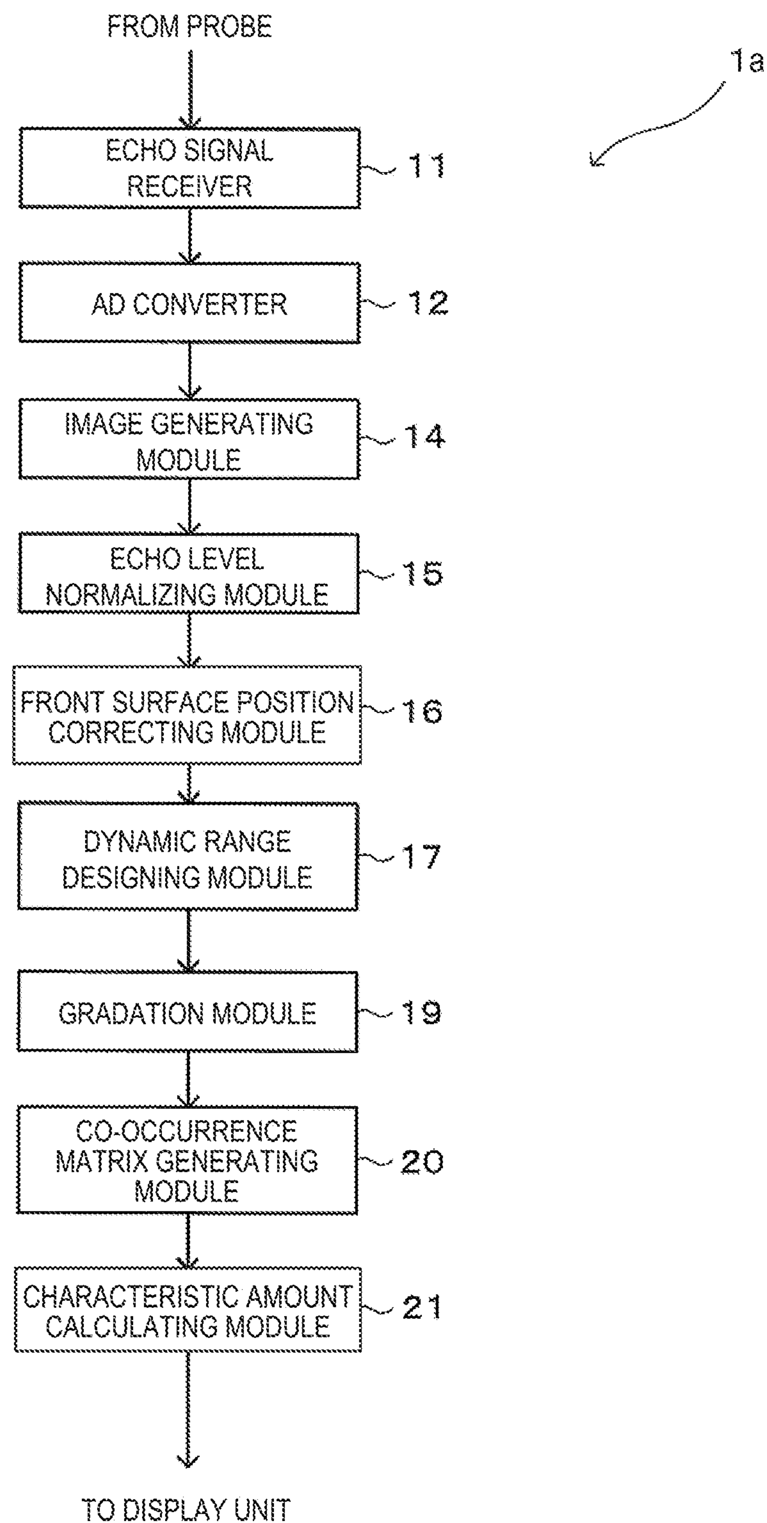
FIG. 15 is a block diagram illustrating a configuration of an ultrasonic diagnosing device according to another modification.

(7) FIG. 15 is a block diagram illustrating a configuration of an ultrasonic diagnosing device 1*a* according to another modification. In the above embodiment, the ultrasonic diagnosing device 1 including the ultrasonic probe 4 and the display unit 5 is exemplarily illustrated; however, without limiting to this, this disclosure may be applied to an ultrasonic diagnosing device in which the ultrasonic probe 4, the display unit 5, etc. are omitted, such as that illustrated in FIG. 15.

(8) In the above embodiment, the echo level image is generated based on the echo signals received by the probe, and the characteristic amounts are calculated based on the echo level image; however, it is not limited to this. Specifically, even without generating the echo level image, the characteristic amounts may be calculated based on the echo intensities of the samples corresponding to the respective positions of the area-of-interest.

Figure 16:
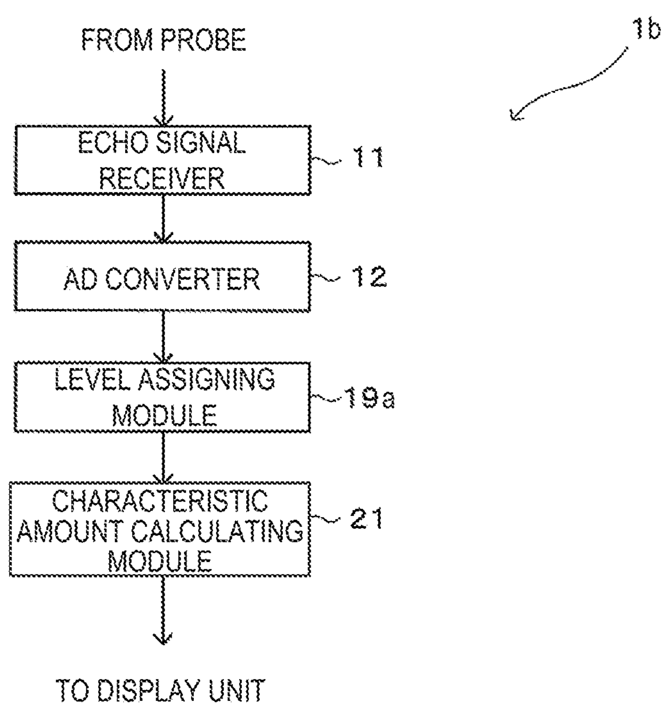
FIG. 16 is a block diagram illustrating a configuration of an ultrasonic diagnosing device according to another modification.

FIG. 16 is a block diagram illustrating a configuration of an ultrasonic diagnosing device 1*b* according to another modification. The ultrasonic diagnosing device 1*b* according to the other modification includes a level assigning module 19*a*. The level assigning module 19*a* assigns each echo intensity to one of a plurality of levels of echo intensities, the echo intensity being an intensity of the echo data outputted by the AD converter 12, and being each of the intensities of the echo data of the samples corresponding to the respective positions of the area-of-interest. By targeting samples which are in a given positional relationship with each other among the samples having the echo intensities assigned to the plurality of levels, the characteristic amount calculating module 21 calculates the characteristic amounts based on a combination of the echo intensities. Note that, when generating the co-occurrence matrixes with the ultrasonic diagnosing device 1*b* according to this modification, the co-occurrence matrixes are generated targeting the pairs of samples corresponding to the area-of-interest, each pair of pixels consisting of a pair of samples having a positional relationship in which they are separated by a given distance in a given direction.

In the above embodiment, the area-of-interest is extracted from the analysis area, and the characteristic amounts are calculated based on the echo data of the samples within the area-of-interest; however, it is not limited to this. Specifically, the entire analysis area may be designed as the area-of-interest, and the characteristic amounts may be calculated based on the echo data of the samples inside the area-of-interest (i.e., the analysis area).

DESCRIPTION OF REFERENCE NUMERALS

1, 1*a*, 1*b* Ultrasonic Diagnosing Device
4 Probe, Ultrasonic Probe
19 Gradation Module (Level Assigning Module)
19*a* Level Assigning Module
21 Characteristic Amount Calculating Module

What is claimed is:

1. An ultrasonic diagnosing device for diagnosing a state of a detected part that is a detection target in a detected body, comprising:

an ultrasonic probe configured to transmit ultrasonic signals into the body, and receive echo signals reflected from the body;

processing circuitry configured to:

calculate a plurality of echo signal intensities at a plurality of positions in an area-of-interest in a two-dimensional plane identified by a depth direction of the body and a scanning direction intersecting the depth direction, based on the echo signals reflected inside the body;

assign each of the plurality of echo signal intensities to one of a plurality of echo intensity levels;

generate two or more targeting pairs of the plurality of echo signal intensities at the plurality of positions, the two or more targeting pairs having a predetermined positional relationship to each other on the two-dimensional plane;

calculate a characteristic amount including a correlation or a contrast of the targeting pairs based on the two or more targeting pairs of the echo signals, wherein the characteristic amount is an index indicating a state of at least one of a cartilage or a knee;

and output the characteristic amount on a display.

2. The ultrasonic diagnosing device of claim 1, wherein the processing circuitry is further configured to generate an echo level image configured with a plurality of pixels having luminance levels corresponding to the intensities of the echo signals that are samples respectively corresponding to the positions of the area-of-interest, the plurality of pixels associated with the respective positions of the area-of-interest, respectively.

3. The ultrasonic diagnosing device of claim 1, wherein the processing circuitry is further configured to set an upper limit echo intensity and a lower limit echo intensity, the upper limit echo intensity indicating a highest value among the echo signal intensities assigned to the plurality of echo intensity levels, the lower limit echo intensity indicating a lowest value among the echo signal intensities assigned to the plurality of echo intensity levels.

4. The ultrasonic diagnosing device of claim 1, wherein the area-of-interest is configured as an area including echo signals from a front surface of the detected part.

5. The ultrasonic diagnosing device of claim 1, wherein the processing circuitry is further configured to generate a co-occurrence matrix based on the echo signal intensities of samples respectively corresponding to the positions of the area-of-interest, the echo signal intensities assigned to the plurality of echo intensity levels by the processing circuitry, wherein the processing circuitry calculates the characteristic amount based on the co-occurrence matrix generated by the processing circuitry.

6. The ultrasonic diagnosing device of claim 5, wherein the processing circuitry calculates, as the co-occurrence matrix, a first co-occurrence matrix targeting pairs of samples corresponding to the area-of-interest, each of the pairs of the samples consisting of a pair of samples having the predetermined positional relationship in which the samples are separated by a given distance in the scanning direction intersecting the depth direction, and wherein the processing circuitry calculates the correlation based on the first co-occurrence matrix.

7. The ultrasonic diagnosing device of claim 5, wherein the processing circuitry calculates, as the co-occurrence matrix, a second co-occurrence matrix targeting pairs of samples corresponding to the area-of-interest, each of the pairs of the samples consisting of a pair of samples having the predetermined positional relationship in which the samples are separated by a given distance in the depth direction, and wherein the processing circuitry calculates the contrast based on the second co-occurrence matrix.

8. The ultrasonic diagnosing device of claim 1, wherein the processing circuitry is further configured to detect a position of a front surface of the detected part in the depth direction based on the echo signals; and wherein the processing circuitry is further configured to determine the area-of-interest having a first given length in the depth direction from a given position of the front surface and a second given length of the front surface in the scanning direction based on the position of the front surface of the detected part detected by the processing circuitry.

9. The ultrasonic diagnosing device of claim 8, wherein the processing circuitry is further configured to set an upper limit echo intensity and a lower limit echo intensity, the upper limit echo intensity indicating a highest value among the echo signal intensities assigned to the plurality of echo intensity levels, the lower limit echo intensity indicating a lowest value among the echo signal intensities assigned to the plurality of echo intensity levels, wherein the processing circuitry detects a highest signal value among the echo signals obtained from the front surface of the detected part detected by the processing circuitry, and sets the highest signal value as the upper limit echo intensity, and the processing circuitry further configured to divide the echo signal intensities at the respective positions of the area-of-interest by the highest signal value detected by the processing circuitry.

10. The ultrasonic diagnosing device of claim 8, wherein the processing circuitry is further configured to correct depth positions of samples corresponding to the area-of-interest in the depth direction so that the position of the front surface of the detected part in the area-of-interest is located within a given depth position in the depth direction.

11. The ultrasonic diagnosing device of claim 1, further comprising:

the ultrasonic probe configured to transmit the ultrasonic signals into the detected body; and a display unit configured to display the characteristic amount calculated by the processing circuitry and the index derived based on the characteristic amount and indicating the state of the detected part of the detected body.

12. The ultrasonic diagnosing device of claim 11, wherein the ultrasonic probe transmits and receives ultrasonic waves in relation to the area-of-interest defined in the depth direction and the scanning direction of the ultrasonic probe, by scanning along a front surface of the detected body, the scanning direction intersecting the depth direction.

* * * * *